United States Patent [19]
Ellingson et al.

[11] Patent Number: 6,136,300
[45] Date of Patent: *Oct. 24, 2000

[54] LONG WEAR NAIL POLISH HAVING ADHESION, TOUGHNESS, AND HARDNESS

[75] Inventors: Peter Christopher Ellingson, Hamilton; Edward Dewey Smith, III, Mason, both of Ohio

[73] Assignee: The Procter & Gamble Company, Cincinnati, Ohio

[*] Notice: This patent is subject to a terminal disclaimer.

[21] Appl. No.: 09/071,273

[22] Filed: May 1, 1998

[51] Int. Cl.⁷ .............................. A61K 6/00; A61K 7/00; A61K 7/04
[52] U.S. Cl. ................................ 424/61; 424/401
[58] Field of Search .................... 424/61, 401; 427/389

[56] References Cited

U.S. PATENT DOCUMENTS

| | | | |
|---|---|---|---|
| 4,277,380 | 7/1981 | Williams et al. | 260/18 |
| 4,384,058 | 5/1983 | Galante | 524/32 |
| 4,431,763 | 2/1984 | Reed | 524/389 |
| 4,442,259 | 4/1984 | Isgur et al. | 524/839 |
| 4,766,005 | 8/1988 | Montgomery et al. | 427/4 |
| 4,812,492 | 3/1989 | Eckes et al. | 523/351 |
| 4,844,102 | 7/1989 | Repensek et al. | 132/17 |
| 5,120,529 | 6/1992 | Koch et al. | 424/61 |
| 5,266,322 | 11/1993 | Myers et al. | 424/401 |
| 5,380,520 | 1/1995 | Dobbs | 424/61 |
| 5,538,717 | 7/1996 | La Poterie | 424/61 |
| 5,607,665 | 3/1997 | Calello et al. | 424/61 |
| 5,681,550 | 10/1997 | Rubino | 424/61 |
| 5,716,603 | 2/1998 | Chen et al. | 424/61 |
| 5,811,084 | 9/1998 | Busch, Jr. et al. | 424/61 |

FOREIGN PATENT DOCUMENTS

| | | |
|---|---|---|
| 87242557 | 8/1987 | Canada . |
| 0 061 348 A1 | of 0000 | European Pat. Off. . |
| 0 022452 A1 | 1/1981 | European Pat. Off. . |
| 0 063467 A1 | 10/1982 | European Pat. Off. . |
| 0 325038 A2 | 7/1989 | European Pat. Off. . |
| 0 418469 A1 | 3/1991 | European Pat. Off. . |
| 0 455373 A1 | 6/1991 | European Pat. Off. . |
| 0 627212 | 5/1993 | European Pat. Off. . |
| 0 619 111 A1 | 12/1994 | European Pat. Off. . |
| 0299758 B1 | 12/1994 | European Pat. Off. . |
| 0 636361 | 2/1995 | European Pat. Off. . |
| 0 637600 A1 | 2/1995 | European Pat. Off. . |
| 0 658609 A1 | 6/1995 | European Pat. Off. . |
| 0 679384 | 11/1995 | European Pat. Off. . |
| 0 680742 A1 | 11/1995 | European Pat. Off. . |
| 0 705594 A1 | 4/1996 | European Pat. Off. . |
| 0 797977 A1 | 10/1997 | European Pat. Off. . |
| 57-23632 | 2/1982 | Japan . |
| 4 103512 | 4/1992 | Japan . |
| 4 103513 | 4/1992 | Japan . |
| 4 103514 | 4/1992 | Japan . |
| 5 148122 | 6/1993 | Japan . |
| 5 155737 | 6/1993 | Japan . |
| 5 310531 | 11/1993 | Japan . |
| 7 309721 | 11/1995 | Japan . |
| 9 157135 | 6/1997 | Japan . |
| 9 268113 | 10/1997 | Japan . |
| 883078 | 11/1981 | U.S.S.R. . |
| WO 92/16185 | 3/1992 | WIPO . |
| WO 92/05762 | 4/1992 | WIPO . |
| WO 96/34061 | 10/1996 | WIPO . |
| WO 97/00664 | 1/1997 | WIPO . |
| WO 97/42930 | 11/1997 | WIPO . |

OTHER PUBLICATIONS

U.S. Ser. No. 09/070,960, Ellingson, et al., filed May 1, 1998.
U.S. Ser. No. 09/071,424, Ellingson, et al., filed May 1, 1998.
U.S. Ser. No. 09/071,098, Ellingson, et al., filed May 1, 1998.
U.S. Ser. No. 09/071,097, Smith, et al., filed May 1, 1998.
U.S. Ser. No. 09/071,423, Ellingson, et al., filed May 1, 1998.
U.S. Ser. No. 09/071,099, Ellingson, et al., filed May 1, 1998.

*Primary Examiner*—Thurman K. Page
*Assistant Examiner*—S. Howard
*Attorney, Agent, or Firm*—Kelly L. McDow-Dunham; Loretta J. Henderson; Michael E. Hilton

[57] ABSTRACT

The present invention relates to kits and films formed from the kits which are useful as cosmetic or therapeutic agents, as well as methods of their use. The films and kits herein are particularly useful as polishes for mammalian nails. More particularly, the present invention relates to kits and films which, when applied to mammalian nails exhibit long wear. When applied to mammalian nails, the present kits provide films exhibiting Peak Adhesive Strengths of greater than about 15 g/mm and exhibiting a Toughness Value of greater than about 1.2 MPa or a Wear Value of greater than about 1000 $(MPa)^2$. The present invention further relates to methods of coating mammalian nails with kits and films formed from the kits which exhibit Peak Adhesive Strengths of greater than about 15 g/mm and exhibit Toughness Values of greater than about 1.2 MPa or Wear Values of greater than about 1000 $(MPa)^2$.

21 Claims, No Drawings

LONG WEAR NAIL POLISH HAVING ADHESION, TOUGHNESS, AND HARDNESS

TECHNICAL FIELD

The present invention relates to kits useful as cosmetic or therapeutic agents and films formed therefrom having defined adhesion and/or toughness properties. The kits and films herein are particularly useful as polishes for mammalian nails.

BACKGROUND OF THE INVENTION

Consumers use nail polishes to cosmetically enhance their nails or protect the nails from everyday conditions and stressors. However, these nail polish compositions are deficient in many respects, including their inability to provide long wear. Nail polishes which are known or currently available often exhibit deterioration, particularly in the form of chipping or peeling, in as few as one or two days. Such poor wear often forces consumers to remove their nail polish soon after original application and reapply additional nail polish to the nails. Consumers may also attempt to correct the unsightly appearance of the deteriorating nail polish by "touching-up" the areas of the nail which exhibit the deterioration, a practice which actually impairs the overall look of the nail polish. Finally, consumers may choose to do nothing about the deterioration and allow, for example, chipping and peeling to progress, resulting in nails which are not only minimally protected from the environment but are unsightly as well.

The art is replete with nail polish compositions which are promoted as having long wear, good adhesion, and/or resistance to chipping. While some nail polish compositions provide better wear than others, a need remains for nail polish compositions providing long wear.

Extreme examples of nail polish compositions which exhibit inadequate adhesion are those which are easily and completely peeled or stripped off the nails without the use of a solvent. See, e.g. EP 0,680,742, Mellul et al., assigned to L'Oreal.

Furthermore, other nail polish compositions are completely removable with water and, therefore, are not practical for normal use and do not provide adhesive and/or long wear properties under everyday conditions. See, e.g., JP 05-155,737, Itsumi et al., assigned to Yuho Chemical Co. Ltd. and EP 0,679,384, Ramin et al., assigned to L'Oreal.

Still further, nail polishes exhibiting moderate or good adhesion to the nail tend not to provide the hardness essential for avoidance of chipping resistance to abrasion. Similarly, known polishes which are tough tend to be too rigid and do not exhibit adequate adhesion to the nail. Without intending to be limited by theory, it is believed that adhesion is promoted by nail polish films which follow movement of the nail (e.g., bending) without cracking or other failure by dissipating energy. Tough films store energy instead of dissipating energy, in essence fighting against adhesion to the nail. Compatibility of these properties has been minimally explored in the nail polish art, resulting in nail polishes having adhesion or toughness/hardness, but not both.

It would therefore be desirable to provide nail polishes having improved wear properties including improved adhesion to the nail and the toughness or hardness essential for deflecting environmental stressors. The present inventors have surprisingly discovered nail polish kits which, when applied to mammalian nails, form films exhibiting both improved adhesion to the nail and improved toughness and/or hardness properties. By virtue of these properties, the present kits provide nail polish films exhibiting long wear at a superior level not provided by the nail polishes which are presently known and used.

SUMMARY OF THE INVENTION

The present invention relates to kits and films formed from application of the kits which, when applied to mammalian nails, exhibit long wear. The present kits comprise two or more compositions, preferably a basecoat composition, a topcoat composition, and, optionally, a midcoat composition. Each composition comprises a film-forming polymer, a liquid diluent, and, optionally, other components. The present film-forming polymers are selected from polyurethanes, polyacryls, polymethacryls, cellulosic polymers, styrene-acryl copolymers, polystyrene-polyacryl mixtures, polysiloxanes, polyesters, urethane-acryl copolymers, siloxane-urethane copolymers, polyurethane-polymethacryl mixtures, silicone-acryl copolymers, vinyl acetate polymers, and mixtures thereof. When applied to mammalian nails, the present kits provide films exhibiting Peak Adhesive Strengths of greater than about 10 g/mm and either Toughness Values of greater than about 1.2 MPa or Wear Values of greater than about 1000 $(MPa)^2$.

DETAILED DESCRIPTION OF THE INVENTION

The essential components of the present invention are herein described below. Also included are non-limiting descriptions of various optional and preferred components useful in the kits of the present invention.

The present invention can comprise, consist of, or consist essentially of any of the required or optional components and/or limitations described herein.

All percentages and ratios are calculated by weight unless otherwise indicated. All percentages are calculated based on the total composition unless otherwise indicated.

All component or composition levels are in reference to the active level of that component or composition, and are exclusive of impurities, for example, residual solvents or by-products, which may be present in commercially available sources.

Referred to herein are trade names for materials including, but not limited to, polymers and optional components. The inventors herein do not intend to be limited by materials under a certain trade name. Equivalent materials (e.g., those obtained from a different source under a different name or catalog (reference) number) to those referenced by trade name may be substituted and utilized in the kits, films, and methods herein.

All documents referred to herein, including all patents, patent applications, and printed publications, are hereby incorporated by reference in their entirety.

The kits and films of the present invention are suitable for use as a nail polish for mammalian nails. As used herein, the term "suitable for use as a nail polish for mammalian nails" means that the compositions, kits, or films thereof are suitable for use in contact with mammalian nails without undue toxicity, incompatibility, instability, allergic response, and the like.

As used herein, the term "nail polish" is a comprehensive term describing a nail polish composition, film, product (including coloring products), system, kit, or the like, which is useful for providing, for example, aesthetic, therapeutic, or prophylactic benefits to the nail.

As used herein, the term "mammalian nail" means a keratinaceous plate present at the upper surface of the end of a finger or toe of a primate, most preferably a human, or the homologous claw or hoof of another mammal.

The layers and films herein may be joined to mammalian nails. As used herein, the terms "joined to", "joined to mammalian nails", or the like means in contact with or applied to a mammalian nail through physical forces in such a manner that the layer or film is contiguous to either the nail itself, a preceding layer, a succeeding layer, or matter previously applied to or existing on the nail. The layer or film may be "joined to" a mammalian nail, preceding layer, or succeeding layer even though other matter (such as another preceding or succeeding layer) intervenes. Accordingly, matter which is "joined to", for example, a mammalian nail, need not actually be contiguous to that mammalian nail.

As used herein, the term "contiguous to" means directly joined to by physical forces through touching and boundary sharing with essentially no intervening matter.

As used herein, the term "film" means one or more layers of a nail polish suitable for use on mammalian nails which forms when one or more compositions of the kit is applied to, and dries on, mammalian nails.

As used herein, the term "layer" means one substantially dry coat of nail polish which forms when a composition of the kit is applied to, and dries on, a mammalian nail.

As used herein, the term "preceding layer" means a layer which is joined to a nail and is closer in proximity to the nail as compared to a reference layer joined to the same nail. For example, wherein a basecoat and a topcoat are joined to a nail, the basecoat is a preceding layer relative to the topcoat. Similarly, wherein a basecoat, midcoat, and topcoat are joined to a nail, the basecoat and midcoat are preceding layers relative to the topcoat, and the basecoat is a preceding layer relative to both the midcoat and topcoat.

As used herein, the term "succeeding layer" means a layer which is joined to a nail and is further in proximity from the nail as compared to a reference layer joined to the same nail. For example, wherein a basecoat and a topcoat are joined to a nail, the topcoat is a succeeding layer relative to the basecoat. Similarly, wherein a basecoat, midcoat, and topcoat are joined to a nail, the midcoat and topcoat are succeeding layers relative to the basecoat, and the topcoat is a succeeding layer relative to both the basecoat and midcoat.

As used herein, the term "substantially dry" in reference to a film or a layer means that the film or layer feels dry, smooth, or not tacky when it is touched with a human fingertip.

Kits and Films of the Present Invention

The kits of the present invention, when applied to mammalian nails, provide films exhibiting long wear as defined by their adhesion and/or toughness, as defined herein. The kits comprise two or more compositions, preferably a basecoat composition, a topcoat composition, and, optionally, a midcoat composition. Each composition comprises a film-forming polymer, a liquid diluent, and, optionally, one or more other suitable components as described herein. As used herein, the term "film-forming polymer" means a homopolymer, copolymer, or mixture thereof which forms an adherent continuum from a composition when applied to mammalian nails. See, e.g., Polymer Colloids, Robert M. Fitch, ed., New York: Plenum Press, pp. 173–183 (1971). As used herein, the term "copolymer" includes linear, block, branched, graft, comb, and star copolymers.

Although the term "film-forming polymer" is used herein to describe a polymer in a composition, in some circumstances, polymerization may not actually take place until application of the composition (to the nail, for example) is performed. Accordingly, as used herein, the term "film-forming polymer" is meant to encompass monomers which have not yet polymerized but will upon application to the nail.

The film-forming polymers herein are preferably self-curing polymers. That is, the preferred polymers do not require chemical reaction or introduction of energy (e.g., exposure to ultraviolet rays) to form the adherent continuum.

The film-forming polymers herein can be selected from nonionic, ionic (anionic or cationic), and amphoteric (including zwitterionic) polymers. Wherein the film-forming polymer is water-borne, the polymer is preferably anionic.

The film-forming polymers herein are preferably, but are not limited to, solvent-borne or water-borne polymers. As used herein, the term "water-borne", with reference to a film-forming polymer, means that the polymer was prepared in a mixture comprising water and is preferably added to the composition which it comprises as a mixture (preferably a dispersion) in water. As used herein, the term "solvent-borne", with reference to a film-forming polymer, means that the polymer was prepared under substantially anhydrous conditions and is preferably added to the composition which it comprises as a substantially anhydrous mixture (preferably a solution).

Preferred film-forming polymers of the present invention are selected from polyurethanes, polyacryls, polymethacryls, cellulosic polymers, styrene-acryl copolymers, polystyrene-polyacryl mixtures, polysiloxanes, polyesters, urethane-acryl copolymers, siloxane-urethane copolymers, polyurethane-polymethacryl mixtures, silicone-acryl copolymers, vinyl acetate polymers, and mixtures thereof. The term "polyacryl" includes polyacrylates, polyacrylics, and polyacrylamides. The term "polymethacryl" includes polymethacrylates, polymethacrylics, and polymethacrylamides. The term "cellulosic polymers" includes all cellulose polymers, including esters thereof.

Examples of preferred polyacryls, polymethacryls, and styrene-acryl copolymers include Gelva® 2497 (commercially available from Monsanto Co., St. Louis, Mo.), Duraplus® 2 (commercially available from Rohm & Haas Co., Philadelphia, Pa.), Joncryl® 95 (commercially available from S.C. Johnson Polymer, Sturtevant, Wis.), SCX-1537 (S.C. Johnson Polymer), SCX-1959 (S.C. Johnson Polymer), SCX-1965 (S.C. Johnson Polymer), Joncryl® 530 (S.C. Johnson Polymer), Joncryl® 537 (S.C. Johnson Polymer), Glascol LS20 (commercially available from Allied Colloids, Suffolk, Va.), Glascol C37 (Allied Colloids), Glascol LS26 (Allied Colloids), Glascol LS24 (Allied Colloids), Glascol LE45 (Allied Colloids), Surcol 441® (Allied Colloids), Carboset® CR760 (commercially available from BFGoodrich, Cleveland, Ohio), Carboset® CR761 (BFGoodrich), Carboset® CR763 (BFGoodrich), Carboset® 765 (BFGoodrich), Carboset® 19X2 (BFGoodrich), Carboset® XL28 (BFGoodrich), Hycar 26084 (BFGoodrich), Hycar 26091 (BFGoodrich), Carbobond 26373 (BFGoodrich), Neocryl® A-601 (commercially available from Zeneca Resins, Wilmington, Mass.), Neocryl® A-612 (Zeneca Resins), Neocryl® A-6044 (Zeneca Resins), Neocryl® A-622 (Zeneca Resins), Neocryl® A-623 (Zeneca Resins), Neocryl® A-634 (Zeneca Resins), and Neocryl® A-640 (Zeneca Resins).

An example of a preferred polysiloxane is PSA 590 (commercially available from General Electric, Waterford, N.Y.).

Examples of preferred urethane-acryl copolymers include Sancure® AU-4000 (commercially available from BFGoodrich), Sancure® AU-4010 (BFGoodrich), Witcobond A-100 (commercially available from Witco Performance Chemicals, Houston, Tex.), Witcobond W-610 (Witco Performance Chemicals), NeoPac R-9000 (commercially available from Zeneca Resins), NeoPac R-9030 (Zeneca Resins), and NeoPac R-9699 (Zeneca Resins).

Preferred polyurethanes are selected from aromatic polyether polyurethanes, aliphatic polyether polyurethanes, aromatic polyester polyurethanes, aliphatic polyester polyurethanes, aromatic polycaprolactam polyurethanes, and aliphatic polycaprolactam polyurethanes. The more preferred polyurethanes are selected from aromatic polyether polyurethanes, aliphatic polyether polyurethanes, aromatic polyester polyurethanes, and aliphatic polyester polyurethanes. Examples of preferred polyurethanes include Sancure 2710® and/or Avalure UR 445® (which are equivalent copolymers of polypropylene glycol, isophorone diisocyanate, and 2,2-dimethylolpropionic acid, having the International Nomenclature Cosmetic Ingredient name "PPG-17/PPG-34/IPDI/DMPA Copolymer"), Sancure 878®, Sancure 815®, Sancure 1301®, Sancure 2715®, Sancure 18280, Sancure 20260, Sancure 1818®, Sancure 853®, Sancure 830®, Sancure 825®, Sancure 776®, Sancure 850®, Sancure 12140®, Sancure 12619®, Sancure 835®, Sancure 843®, Sancure 898®, Sancure 899®, Sancure 1511®, Sancure 1514®, Sancure 1517®, Sancure 1591®, Sancure 2255®, Sancure 2260®, Sancure 2310®, Sancure 2725®, and Sancure 12471® (all of which are commercially available from BFGoodrich, Cleveland, Ohio), Bayhydrol DLN (commercially available from Bayer Corp., McMurray, Pa), Bayhydrol LS-2033 (Bayer Corp.), Bayhydrol 123 (Bayer Corp.), Bayhydrol PU402A (Bayer Corp.), Bayhydrol 110 (Bayer Corp.), Witcobond W-320 (commercially available from Witco Performance Chemicals), Witcobond W-242 (Witco Performance Chemicals), Witcobond W-160 (Witco Performance Chemicals), Witcobond W-612 (Witco Performance Chemicals), Witcobond W-506 (Witco Performance Chemicals), NeoRez R-940 (commercially available from Zeneca Resins), NeoRez R-960 (Zeneca Resins), NeoRez R-962 (Zeneca Resins), NeoRez R-966 (Zeneca Resins), NeoRez R-967 (Zeneca Resins), NeoRez R-972 (Zeneca Resins), NeoRez R-9409 (Zeneca Resins), NeoRez R-9637 (Zeneca), NeoRez R-9649 (Zeneca Resins), and NeoRez R-9679 (Zeneca Resins).

Preferred solvent-borne polyurethanes include Sanres EX499® (hexylene glycol/neopentyl glycol/isophorone diisocyanate copolymer, Sanres 12711®, Sanres 6010®, and Sanres 6012® (all of which are available from BFGoodrich). The most preferred solvent-borne polyurethane is Sanres EX499®.

Examples of preferred water-borne polyester polyurethanes include Sancure® 2060 and Sancure® 815 (both of which are commercially available from BFGoodrich).

The most preferred water-borne polyurethanes are aliphatic polyether polyurethanes. Examples of preferred aliphatic polyether polyurethanes include Sancure 2710® and/or Avalure UR 445®, Sancure 878®, NeoRez R-966, NeoRez R-967, and Witcobond W-320.

Preferred cellulosic polymers include, for example, nitrocellulose, cellulose acetate butyrate, and cellulose acetate propionate. The most preferred cellulosic polymer is nitrocellulose. Exemplary nitrocellulose polymers are nitrocellulose RS types (nitrogen content of 11.5% to 12.2%), commercially available from Hercules, such as nitrocellulose RS ½ second, nitrocellulose RS ¼ second, nitrocellulose RS ⅛ second, and nitrocelluose RS 1/16 second, and the like. Wherein a composition comprises a cellulosic polymer, the composition preferably comprises a plasticizer.

The compositions of the present invention further comprise a carrier comprising a liquid diluent. The liquid diluent comprises water, organic solvent, or mixtures thereof. Preferred organic solvents include those which are volatile. Preferred volatile organic solvents, at atmospheric pressure, have a boiling point of from about 50° C. to about 140° C., more referably from about 56° C. to about 125° C., and most preferably from about 56° C. to about 98° C. Wherein the film-forming polymer utilized is water-borne, the organic solvent is preferably water-miscible.

Preferred organic solvents are selected from alcohols, esters, ketones, aromatic hydrocarbons, aliphatic hydrocarbons, ethers, and mixtures thereof. Alcohols and esters are more preferred. Preferred alcohols are monohydric. The most preferred monohydric alcohols are ethanol, iso-propanol, and n-propanol. The most preferred esters are ethyl acetate and butyl acetate. Other non-limiting examples of suitable organic solvents are benzyl alcohol, amyl acetate, propyl acetate, acetone, heptane, iso-butyl acetate, isopropyl acetate, toluene, methyl acetate, iso-butanol, n-amyl alcohol, n-butyl alcohol, hexane, and methyl ethyl ketone.

The kits of the present invention may further comprise information which informs a user of the kit, by words, pictures, and/or the like, that use of the kit will provide one or more long wear benefits, including, but not limited to, resistance to chipping, peeling, denting, and/or peeling.

The films herein are formed when a kit of the present invention is applied to mammalian nails. The films of the present invention comprise two or more layers formed from two or more different compositions, most preferably two or three layers formed from two or three different compositions, respectively. The preferred films are those which are comprised of a basecoat and a topcoat, and those which further comprise a midcoat.

The multi-layer films herein form when two or more compositions of the kit, as described herein, are applied to and substantially dry on mammalian nails. The compositions useful herein may be described as basecoat compositions, midcoat compositions, or topcoat compositions, depending on their intended positioning on the nail.

A. Basecoat Compositions

As used herein, a "basecoat composition" is a composition which is suitable for application to a mammalian nail to form a basecoat, which is a layer of nail polish. A basecoat composition is preferably applied contiguously to a mammalian nail with or without, more preferably with, one or more succeeding layers applied to the resulting basecoat. The basecoat composition is preferably applied contiguously to a mammalian nail with one or more, more preferably one (topcoat), and most preferably two (midcoat and topcoat), succeeding layers joined to the resulting basecoat.

Without intending to be limited by theory, it is believed that the basecoats of the present invention are beneficial to long wear because they provide a preferred level of adhesion to the nail, as described herein. Such adhesion is believed to be due to physical forces, rather than chemical bonding to the nail. As is known in the art, these physical forces include non-covalent interactions such as polar, non-polar, hydrogen bonding, and charged interactions as well as physical interactions such as mechanical interlocking. Preferred basecoat compositions of the present invention provide, in combination with other compositions as described herein, films exhibiting Peak Adhesive Strengths of greater than about 10 g/mm, more preferably greater than about 15 g/mm, even more preferably greater than about 25 g/mm, and most preferably greater than about 50 g/mm.

Without intending to be limited by theory, the Peak Adhesive Strengths defined herein are largely achieved via the surface energies and/or polarities of the layer of the film which is contiguous to the nail (i.e., the basecoat). Adhesion may be optimized by matching the surface energy and/or polarity of the basecoat to that of the nail, which have been found by the present inventors to be surface energies from about 32 mN/m to about 43 mN/m, more preferably from about 34 mN/m to about 42 mN/m, and polarities from about 0.19 to about 0.29, more preferably from about 0.20 to about 0.24.

Such matching is primarily achieved by selection of the film-forming polymer. Formulation adjustments which may change surface energies and/or polarities of the final film may reduce adhesion between the nail surface and the film-forming polymer in the basecoat. Thus, the film-forming polymer itself is selected, first by general class (polyurethane, polyacryl, e.g) and second via the chemistry of the monomers present in the film-forming polymer. Preferred polymer classes which achieve the presently defined surface energies and polarities are defined herein. Experimentation within a polymer class, which is well within the purview of the ordinarily skilled artisan, may be utilized to select film-forming polymers having surface energies and polarities which most closely match the defined ranges.

The present basecoat compositions comprise a film-forming polymer, a liquid diluent, and, optionally, one or more other suitable components as described herein. The basecoat compositions preferably comprise from about 0.1% to about 40%, more preferably from about 1% to about 10%, and most preferably from about 2% to about 6% of the film-forming polymer (polymer solids), and preferably from about 10% to about 90%, more preferably from about 40% to about 90%, even more preferably from about 50% to about 90%, and most preferably from about 70% to about 90% of the volatile organic solvent (as described herein above), by weight of the composition. Preferably, the balance of the compositions is substantially water, preferably at least about 4%, more preferably from about 4% to about 85%, still more preferably from about 10% to about 80%, and most preferably from about 25% to about 80%, by weight of the composition, of water.

The film-forming polymers of the basecoat compositions are preferably water-insoluble at ambient temperature and pressure.

Preferred film-forming polymers for use in the basecoat compositions are selected from polyurethanes, polyacryls, polymethacryls, urethane-acryl copolymers, styrene-acryl copolymers, cellulosic polymers, polysiloxanes, and mixtures thereof. The more preferred polymers of basecoat compositions are selected from cellulosic polymers, polyurethanes, polyacryls, polymethacryls, polysiloxanes, and mixtures thereof. Even more preferred polymers of basecoat compositions are selected from polyurethanes, polyacryls, polymethacryls, urethane-acryl copolymers, styrene-acryl copolymers, and mixtures thereof. The most preferred polymers for use in the basecoat compositions are polyurethanes. The most preferred polyurethane for use in basecoat compositions is Sancure 2710® and/or Avalure UR 445®. Preferred types of each of these polymer classes, and examples thereof, are described herein above.

Preferred polyacryls, polymethacryls, and styrene-acryl copolymers for use in the basecoat compositions are those having a glass transition temperature ($T_g$) of from about −30° C. to about +60° C., more preferably from about −20° C. to about +20° C.

The most preferred polyacryls and polymethacryls for use in basecoat compositions include Glascol LS20, Glascol C37, Joncryl® 95, and SCX-1965.

The film-forming polymers of the basecoat compositions are preferably solvent-borne or water-borne, most preferably water-borne. Especially preferred are water-borne polymers selected from polyurethanes, polyacryls, polymethacryls, urethane-acryl copolymers, styrene-acryl copolymers, and mixtures thereof.

B. Topcoat Compositions

As used herein, a "topcoat composition" is a composition which is suitable for application to a mammalian nail to form a topcoat, which is a layer of nail polish. The topcoat composition is preferably applied contiguously to, or applied to, one or more preceding layers. The topcoat composition is more preferably applied contiguously to one or two, preferably one (basecoat), and most preferably two (basecoat and midcoat), preceding layers.

Without intending to be limited by theory, it is believed that the topcoats are beneficial to long wear because they deflect environmental stressors by virtue of their toughness and/or hardness, as described herein. The toughness and/or hardness a film exhibits is an indication of, for example, its capability to absorb energy or to experience deformation with minimized fracture. For nail polish, this is an important element of resistance to deterioration. When applied to mammalian nails, a nail polish film will typically and repeatedly experience bending, impact, and abrasion against other surfaces. A nail polish which is tough, such as the topcoats described herein, will resist failure of the film under these abuses, thus providing longer wear on nails. The properties of toughness and hardness is most useful for topcoats because topcoats come into direct contact with the environment. Accordingly, topcoats exhibit the greatest need for resistance to cohesive failure. Preferred topcoats of the present invention exhibit a Toughness Value, as described herein, of greater than about 1.2 MPa, more preferably greater than about 1.8 MPa, even more preferably greater than about 2 MPa, and most preferably greater than about 3.5 MPa, or exhibit a Wear Value, as described herein, of greater than about 1000 $(MPa)^2$, more preferably greater than about 1250 $(MPa)^2$, even more preferably greater than about 1500 $(MPa)^2$, and most preferably greater than about 2000 $(MPa)^2$.

Without intending to be limited by theory, a tough or hard topcoat may be chosen which exhibits strong frequency dependence of its dry film properties, for example G' and G", over a frequency range of $10^{-04}$ to $10^{+01}$ Hz, thus allowing the topcoat to behave as a (flexible) solid under conditions representative of external wear (e.g., tapping and dragging), but to dissipate viscous energy under conditions such as bending. Properties such as G' and G" are easily measured by one knowledgeable in coatings physical measurements, and are described in detail in many textbooks on the subject.

See e.g., *Mechanical Properties of Polymers and Composites*, second ed., Ch. 4 ("Dynamic Mechanical Properties"), Marcel Dekker, Inc. An exemplary composition is set forth in Example 3 herein below which has been found to have nearly ideal rigidity at $10^{+01}$ Hz after 24 to 48 hours of drying on the nail and to have complementary viscous (i.e., G") properties at frequencies below $10^{03}$ Hz, as measured on a Perkin Elmer DMA Model with 100 micron thick films measured at 24 and 48 hours of aging, such as described in *Mechanical Properties of Polymers and Composites*, and especially in the references in Chapter 4 ("Dynamic Mechanical Properties").

The present topcoat compositions comprise a film-forming polymer, a liquid diluent, and, optionally, other suitable components as described herein.

The film-forming polymers of the topcoat compositions are preferably either solvent-borne or water-borne and are preferably water-insoluble. Preferred film-forming polymers for topcoat compositions have glass transition temperatures ($T_g$) from about +20° C. to about +100° C., more preferably from about +30° C. to about +80° C.

The preferred film-forming polymers of topcoat compositions of the present invention are selected from polyurethanes, polyacryls, polymethacryls, styrene-acryl copolymers, cellulosic polymers, polyesters, vinyl acetate polymers, polysiloxanes, polystyrene-polyacryl mixtures, siloxane-urethane copolymers, polyurethane-polymethacryl mixtures, silicone-acryl copolymers, and mixtures thereof. The more preferred film-forming polymers of topcoat compositions are selected from cellulosic polymers, polyurethanes, polyacryls, polymethacryls, polysiloxanes, and mixtures thereof. Even more preferred film-forming polymers of topcoat compositions are selected from polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof. The most preferred film-forming polymers of topcoat compositions are polyacryls and polyurethane-cellulosic polymer mixtures. The most preferred polyacryl for use in topcoat compositions is Duraplus 2®. Preferred types of each of these polymer classes, and examples thereof, are referred to herein above.

Preferred solvent-borne film-forming polymers include polyurethane-polymethacryl mixtures, polyurethane-cellulosic polymer mixtures, polyurethanes, polyacryls, polymethacryls, silicone-acryl copolymers, and mixtures thereof, more preferably, polyacryls and polyurethane-cellulosic polymer mixtures, and most preferably polyacryls.

Wherein the film-forming polymer of the topcoat composition is solvent-borne, the topcoat composition preferably comprises from about 1% to about 50%, more preferably from about 10% to about 25% of the film-forming polymer (polymer solids), by weight of the composition. The topcoat composition comprising the solvent-borne polymer preferably further comprises from about 50% to about 99%, more preferably from about 75% to about 90%, by weight of the composition, of a volatile organic solvent (as described herein above).

Wherein the topcoat composition comprises a solvent-borne film-forming polymer, preferred optional components include thickeners, plasticizers, pigments or dyes, resins, and slip aids.

Preferred water-borne film-forming polymers are selected from polyurethanes, polyacryls, polymethacryls, styrene-acryl copolymers, siloxane-urethane copolymers, and mixtures thereof. More preferred water-borne film-forming polymers are selected from polyacryls and styrene-acryl copolymers and the most preferred water-borne film-forming polymers are polyacryls.

Wherein the film-forming polymer of the topcoat composition is water-borne, the topcoat composition preferably comprises from about 1% to about 40%, more preferably from about 5% to about 30%, and most preferably from about 10% to about 25%, by weight of the composition, of the film-forming polymer (polymer solids).

The topcoat composition comprising the water-borne polymer preferably further comprises a coalescent. Preferably, the topcoat composition comprising the water-borne polymer comprises from about 0.1% to about 30%, more preferably from about 1% to about 20%, by weight of the composition, of a coalescent. Preferably, the ratio of water-borne film-forming polymer to coalescent is from about 1:1 to about 4:1.

Wherein the topcoat composition comprises a water-borne film-forming polymer, other preferred optional components include plasticizers, slip aids (especially waxes and surfactants containing siloxanes), thickeners, and pigments or dyes. Topcoat compositions comprising water-borne film-forming polymers may also optionally contain up to about 50%, more preferably from about 5% to about 40%, and most preferably from about 10% to about 30%, by weight of the composition of a volatile organic solvent. Preferred organic solvents are described herein above.

Wherein the topcoat composition comprises a water-borne polymer, the balance of the composition is substantially water.

The film-forming polymers of the present topcoat compositions may be cross-linked polymers. The present inventors have surprisingly discovered that film-forming polymers which are cross-linked provide properties which are particularly advantageous for topcoat compositions and topcoats including, for example, chip-resistance and superior hardness. Cross-linking may occur either in the composition itself or after application and film formation. However, as used herein, polymers which are not actually cross-linked in the composition but may become cross-linked (ie., "cross-linkable" polymers) due to the presence of a basic moiety (as described herein) are referred to herein as cross-linked polymers.

As used herein, a "cross-linked polymer" is a polymer which is ionically linked either intramolecularly to itself and/or intermolecularly to one or more other polymers wherein the linkage is formed through an ionic bridge between a metallic ion and a basic moiety comprising the polymer. Cross-linked polymers are preferably intermolecularly linked. Suitable metallic ions include those with an oxidation state of +2, +3, +4 or higher and which are soluble in water. Preferred metallic ions are selected from $Zn^{+2}$, $Mg^{+2}$, $Ca^{+2}$, $Fe^{+2}$, $Fe^{+3}$, $Al^{+3}$, $Mn^{+2}$, $Co^2$, and $Ni^{+2}$. More preferred metallic ions are selected from $Zn^{+2}$, $Mg^{+2}$, $Ca^{+2}$, $Fe^{+2}$, $Fe^{+3}$, and $Al^{+3}$. The most preferred metallic ion is $Zn^{+2}$.

The basic moieties herein are negatively charged or otherwise basic. The basic moieties may be either present in, or pendant from, the film-forming polymer backbone. Preferred basic moieties are selected from carboxylates, sulfonates, sulfates, phosphates, phosphonates, hydroxymates, borate esters, imidazoles, α-thioketones, thioacids, and alkyl amines. More preferred basic moieties are selected from carboxylates, sulfonates, sulfates, phosphates, phosphonates, and alkyl amines. Even more preferred basic moieties are selected from carboxylates, sulfonates, sulfates, phosphates, and phosphonates. The most preferred basic moieties are carboxylates.

The most preferred cross-linkable polymers are selected from polyacryls, polymethacryls, styrene-acryl copolymers, styrene-methacryl copolymers, and mixtures thereof. Cross-linked polymers may be commercially obtained (for example, Duraplus 2®). Cross-linked polymers may alternatively be produced by obtaining or synthesizing a polymer comprising a pendant basic moiety and adding to that polymer a metal ion solution such as, for example, Zinc Oxide Solution #1 (containing about 15% metal ion solids, commercially available from S.C. Johnson & Sons, Inc.) or Bacote 20 (commercially available from Magnesium Elektron, Inc., Flemington, N.J.). Wherein a metal ion solution is added, the solution is added in an amount sufficient to react substantially completely with the available basic moieties present on the film-forming polymer. Preferably, the amount of metal ion solids, relative to the polymer solids present in the composition, is from about 0.2% to about 0.7%, more preferably from about 0.3% to about 0.6%, and most preferably from about 0.4% to about 0.5%, by weight of the composition.

Wherein the film-forming polymer is cross-linked, the polymer is most preferably water-borne.

Wherein a topcoat comprises a cross-linked polymer, the topcoat may be removed from the nail by a wash treatment with a chelator solution which selectively pulls metal cross-linking ions out of the film and destroys the film. Suitable chelator solutions are selected based on the type of metal ion utilized. Exemplary solutions include, for example, aqueous solutions of ethylenediamine disuccinic acid.

C. Midcoat Compositions

As used herein, a "midcoat composition" is a composition which is suitable for application to a mammalian nail to form a midcoat, which is a layer of nail polish. The midcoat composition is preferably applied contiguously to a preceding layer, either a basecoat or another midcoat, most preferably a basecoat. One or more succeeding layers is applied to the layer formed by the midcoat composition. Preferably, a topcoat is applied contiguously to the layer formed by the midcoat composition.

The use of midcoats is preferred wherein there are significant differences between the physical and/or mechanical properties of the basecoat and the topcoat. For example, midcoats preferably relax stress between flexible basecoats and tough topcoats and/or provide color.

The present midcoat compositions comprise a film-forming polymer, a liquid diluent, and, optionally, other suitable components as described herein. Preferred optional components for midcoat compositions are selected from plasticizers, pigments, and dyes.

Midcoat compositions preferably comprise from about 10% to about 25%, more preferably from about 10% to about 18% of a film-forming polymer, from about 60% to about 85%, more preferably from about 60% to about 80% of a volatile organic solvent (as described herein above), and preferably 0% to about 13%, more preferably from about 5% to about 13%, and most preferably from about 6% to about 12% of a plasticizer, by weight of the composition.

Film-forming polymers comprising the midcoat compositions are selected from cellulosic polymers, polyurethanes, polyacryls, polymethacryls, polysiloxanes, and mixtures thereof. More preferred film-forming polymers are polyacryls and cellulosic polymers, with cellulosic polymers being the most preferred. Preferred types of each of these polymer classes, and examples thereof, are described herein above.

Preferred polyacryls for the midcoat compositions are those which are hydrophobic and/or exhibit a glass-transition temperature ($T_g$) of from about $-10°$ C. to about $+30°$ C. Wherein the polyacryl has a $T_g$ higher than about $+30°$ C., the midcoat composition preferably comprises a plasticizer.

Exemplary compositions suitable for use as midcoat compositions are commercially available such as, for example, those marketed under the Max Factor® or Cover Girl® trade names.

Optional Components

The compositions of the kits of the present invention may, independently, comprise additional optional components to enhance their performance as a nail polish. For example, antifoams, buffers, chelating agents, coalescents, dispersing agents, dyes, epoxies, fillers, pigments, preservatives, resins, therapeutic and prophylactic agents, thickeners, wax additives, wetting agents, and the like can be included in the compositions herein. Such optional components may be dispersed, solubilized, or otherwise mixed in the carrier and/or the liquid diluent of the compositions. These components may be added to the compositions herein provided they do not substantially hinder the long wear of the kits. Non-limiting examples of optional components are given below.

Coalescents

Coalescents may optionally be added to the compositions to enhance film-formation, most preferably wherein the film-forming polymer is water-borne. Such coalescing aids are known in the art and are typically glycol ethers or glycol ether esters such as $C_{1-10}$ straight or branched chain alkyl glycol alkyl ethers, $C_{1-10}$ straight or branched chain alkyl ether acetates, di-$C_{1-10}$ alkyl ether acetates, and $C_{1-10}$ alkyl glycol phenyl ethers. Preferred coalescing aids include, for example, ethylene glycol ethers (e.g., Dowanol EB®, commercially available from Dow Chemical Co.), diethylene glycol ethers, triethylene glycol ethers, propylene glycol ethers (e.g., Dowanol PnP®, Dow Chemical Co.), dipropylene glycol ethers (e.g., Dowanol DPnP®, Dow art Chemical Co.), tripropylene glycol ethers, terpenes, camphor, methyl cellusolve, butyl cellusolve, hexyl cellusolve, methyl carbitol, butyl carbitol, and dibutyl phthalate.

Preferably, a composition comprises from 0% to about 10%, more preferably from about 0. 1% to about 10%, by weight of the composition, of a coalescent.

Pigments or Dyes

Pigments and other suitable coloring agents, such as dyes, may be incorporated into the compositions. Suitable pigments are inorganic or organic pigments known as, for example, the FD&C and D&C colors, lakes, and iron oxides. Such pigments are disclosed in the C.T.F.A. *Cosmetic Ingredient Handbook*, First Edition, 1988. Organic pigments include, for example, D and C Red, Nos. 10, 11, 12, and 13, D and C Red No. 7, D and C Red Nos. 5 and 6, D and C Red Nos. 30 and 34, lacquers such as D and C Yellow No. 5 and D and C Red No. 2, and guanine. Inorganic pigments include, for example, titanium dioxide, bismuth oxychloride, brown iron oxide, and the red iron oxides.

Preferably, the present compositions comprise from 0% to about 5%, more preferably from 0% to about 2%, and most preferably from 0% to about 1%, by weight of the composition, of a pigment or dye.

Plasticizers

Without intending to be limited by theory, plasticizers cause a composition to become more easily deformed. One or more plasticizers may optionally be added to the present compositions. Suitable plasticizers include those disclosed in WO 97/00664, Chen et al, assigned to Eastman Chemical Co. Suitable plasticizers include phthalates, nonionic surfactant polymers, camphor, castor oil, sucrose acetate isobutyrate, alkyl toluenesulfonamides, e.g., ethyl toluenesulfonamide (e.g., Uniplex PX-45, commercially available from Unitex Chemical Corp., Greenboro, N.C.), and polyesters (e.g., Uniplex 670P, commercially available from Unitex Chemical Corp.), particularly polyester acid derivatives di- and tri-acids. Preferred plasticizers include diethyl phthalate, dibutyl phthalate, dioctyl phthalate, diethyl tartrate, dibutyl tartrate, diethyl phosphate, dibutyl phosphate, polyester sebacates, such as Paraplex G-25® (commercially available from C. P. Hall, Bedford Park, Ill.) polyester adipates, such as Paraplex G-50® (C. P. Hall) and tetraethylene glycol di-2-ethylhexoate, available as Tegmer® (C. P. Hall). The most preferred plasticizers include dibutyl phthalate, Paraplex G-25®, Paraplex G-50®, camphor, Uniplex PX-45, and Tegmer®.

A composition preferably comprises from 0% to about 15%, more preferably from 0% to about 10%, and most preferably from 0% to about 5%, by weight of the composition, of a plasticizer.

Preservatives

One or more preservatives may optionally be added to the present compositions to prevent, inhibit, or retard microbial growth in the composition. Preferred preservatives include methyl paraben, ethyl paraben, propyl paraben, benzyl alcohol, benzoic acid, benzoates (preferably sodium benzoate), sorbates (preferably potassium sorbate), sodium dehydroacetate, 1-(3-chloroallyl)-3,5,7-triaza-1-azoniaadamantane chloride (which may be obtained commercially as Quaternium-15® from Dow Chemical Co., Midland, Mich.), a mixture of 95% 1,3-dimethylol-5,5-dimethyl hydantoin and 5% 3-iodo-2-propynyl butyl carbamate (which mixture is commercially available as Glydant Plus® from Lonza, Inc., Fair Lawn, N.J.), 1,3-dimethylol-5,5-dimethyl hydantoin (commercially available as Glydant® from Lonza, Inc.), diazolidinyl urea (commercially available as Germall II® from Sutton Laboratories, Chatham, N.J.), imidazolidinyl urea (commercially available as Germall 115® from Sutton Laboratories), phenoxyethanol, and Kathon® (commercially available from Rohm and Haas Co., Philadelphia, Pa.). The most preferred preservatives include methyl paraben, ethyl paraben, propyl paraben, benzyl alcohol, benzoic acid, benzoates (preferably sodium benzoate), sorbates (preferably potassium sorbate), and sodium dehydroacetate.

A composition preferably comprises from 0% to about 10%, more preferably from 0% to about 5%, and most preferably from 0% to about 1%, by weight of the composition, of a preservative.

Resins

Resins including, for example, epoxies and polyacrylics, may optionally be added. Examples of suitable resins include Polytex E75® (commercially available from Estron Chemical, Inc., Calvert City, Ky.) and Acryloid B66® (commercially available from Rohm and Haas, Philadelphia, Pa.).

A composition preferably comprises from 0% to about 15%, more preferably from about 0.5% to about 10%, by weight of the composition, of a resin.

Slip Aids

Slip aids may optionally be added to improve surface friction, water resistance, abrasion resistance, and mechanical properties. Slip aids which may be used include wax additives including, for example, animal, fossil, vegetable, mineral, or synthetic waxes. Preferred wax additives include beeswax, carob, candelilla, ozocerite, polyethylene waxes, paraffin waxes, polypropylene waxes, polytetrafluoroethylene (commercially available as Teflon® from DuPont, Wilmington, Del.), nylons, and polyamides. Specifically, preferred wax additives include, but are not limited to, Jonwax® 26 (commercially available from S.C. Johnson Polymer, Sturtevant, Wis.) Jonwax® 120 (S. C. Johnson Polymer), Chemcor 325N35, Chemcor 43N40, Glaswax® E-1 (commercially available from Allied Colloids, Suffolk, Va), Glaswax E-1235 (Allied Colloids), Drewaxo E-3030 (commercially available from Ashland Chemical, Boontown, N.J.), Drewax® E-7030 (Ashland Chemical), Lanco® PP1362D (commercially available from Lubrizol, Wichliffe, Ohio), Lanco® A1601 (Lubrizol), and Lanco® TF1780 (Lubrizol).

Other slip aids include materials containing silicone such as copolymers of polyether and polysiloxane. Examples of such slip aids include, for example, Glide 450 and Abil B-8830 (both of which are commercially available from Goldschmidt Chemical, Hopewell, Va.).

The present compositions preferably comprise from 0% to about 10%, more preferably from about 0.1% to about 10%, even more preferably from about 0.5% to about 8%, and most preferably from about 0.5% to about 3% of a slip aid.

Stabilizers

One or more stabilizers may be added to the compositions herein, e.g., to prevent pigment from settling or to achieve desired application properties. Preferably, stabilizers are added to compositions comprising a solvent-borne film-forming polymer. Preferred stabilizers include clays, e.g., organically modified bentonites and hectorites such as stearalkonium bentonite and stearalkonium hectorite (commercially available from Rheox, Inc., Hightstown, N.J.).

Wherein a stabilizer is added, the composition preferably comprises from about 0.25% to about 3%, still more preferably from about 0.25% to about 2.5%, and most preferably from about 1% to about 2% of the stabilizer, by weight of the composition.

Therapeutic and Prophylactic Agents

Therapeutic and/or prophylactic agents such as, for example, vitamins, proteins, anti-fungal and anti-microbial agents, and sunscreens (including UV-A, UV-B, and broad spectrum solar filters) may optionally be added to the present compositions for the further care and protection of the nails.

Thickeners

Thickeners may optionally be added to the compositions and films herein to achieve desired rheology and application properties. Preferably, thickeners are utilized wherein the composition comprises a water-borne film-forming polymer or at least 4% water. Preferred thickeners include hydroxyethyl cellulose, hydroxypropyl cellulose, methyl cellulose, and other conventional cellulosic polymers, associative thickeners (e.g., hydrophobically modified cellulosic polymers, nonionic urethanes, and alkali swellable urethanes) including Aculyn® 44 (commercially available from Rohm & Haas, Philadelphia, Pa.), clays (e.g., laponite and hydrophilic montmorillonite (commercially available as Bentone® from Rheox, Hightstown, N.J.), and natural rubbers and gums (e.g., guar gum, quaternized guar gum sold under the name Jaguar® C-13-S by Rhone-Poulenc, Shelton, Conn.), hydroxypropyl guar gum, gum arabic, carob gum, carrageenan, and xanthan gum).

The present compositions preferably comprise from 0% to about 10%, more preferably from about 0.1% to about 10%, and even more preferably from about 0.1% to about 5% of a thickener, by weight of the composition.

Preferred Kits of the Present Invention

The kits herein are comprised of two or more separate and different compositions, most preferably two or three separate and different compositions. Preferably, the kits are comprised of at least one of a basecoat composition, a midcoat composition, and/or a topcoat composition. More preferably, the kits are comprised of a basecoat composition, a topcoat composition, and, optionally, a midcoat composition.

A preferred kit ("Kit 1") having two separate and different compositions comprises a basecoat composition and a topcoat composition. The basecoat composition of Kit 1 comprises a film-forming polymer, preferably a water-insoluble polymer, which is selected from polyurethanes, polyacryls, polymethacryls, urethane-acryl copolymers, styrene-acryl copolymers, and mixtures thereof. The topcoat composition of Kit 1 comprises a film-forming polymer, preferably a water-insoluble polymer, which is selected from polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

Another preferred kit ("Kit 2") having three separate and different compositions comprises the basecoat composition and topcoat composition as described for Kit 1, and further comprises a midcoat composition. The midcoat composition of Kit 2 comprises a film-forming polymer, preferably a water-insoluble polymer, which is selected from cellulosic polymers, polyurethanes, polyacryls, polymethacryls, polysiloxanes, and mixtures thereof.

Another preferred kit ("Kit 3") having two separate and different compositions comprises a basecoat composition and a topcoat composition. The basecoat composition of Kit 3 comprises a film-forming polymer, preferably a water-insoluble polymer, which is selected from polyurethanes, polyacryls, polymethacryls, urethane-acryl copolymers, styrene-acryl copolymers, and mixtures thereof. The topcoat composition of Kit 3 comprises a film-forming polymer, preferably a water-insoluble polymer, which is selected from cellulosic polymers, polyurethanes, polyacryls, polymethacryls, polysiloxanes, and mixtures thereof.

Another preferred kit ("Kit 4") having two separate and different compositions comprises a basecoat composition and a topcoat composition. The basecoat composition of Kit 4 comprises a film-forming polymer, preferably a water-insoluble polymer, which is selected from cellulosic polymers, polyurethanes, polyacryls, polymethacryls, polysiloxanes, and mixtures thereof. The topcoat composition of Kit 4 comprises a film-forming polymer, preferably a water-insoluble polymer, which is selected from polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

Method of Making and Using

The compositions of the present invention are made using conventional formulation and mixing techniques. A layer of nail polish may be prepared by standard application of a composition to mammalian nails using a standard brush-applicator as is commonly utilized in the art and removing sufficient liquid diluent (through evaporation of volatiles, most preferably at ambient pressures and temperatures) to form the substantially dry layer. The multi-layer films of the present invention are prepared in a similar manner by standard application of one or more additional compositions contiguously to the preceding layer. Such application is well-known in art.

The present invention includes a method of coating mammalian nails with a nail polish film, wherein the film comprises two or more layers. The method comprises the steps of:

(i) applying a basecoat composition contiguously to the nail, wherein the basecoat composition comprises a film-forming polymer and a liquid diluent;

(ii) removing sufficient liquid diluent from the basecoat composition to form a substantially dry basecoat;

(iii) optionally applying a midcoat composition to the basecoat, wherein the midcoat composition comprises a film-forming polymer and a liquid diluent;

(iv) removing sufficient liquid diluent from the midcoat composition to form a substantially dry layer;

(v) applying a topcoat composition to the basecoat (or the layer formed by the midcoat composition, if used), wherein the topcoat composition comprises a film-forming polymer and a liquid diluent; and (vi) removing sufficient liquid diluent from the topcoat composition to form a substantially dry topcoat;

wherein the film exhibits a Peak Adhesive Strength of greater than about 10 g/mm, more preferably greater than about 15 g/mm, even more preferably greater than about 25 g/mm, and most preferably greater than about 50 g/mm and the topcoat exhibits a Toughness Value, as described herein, of greater than about 1.2 MPa, more preferably greater than about 1.8 MPa, even more preferably greater than about 2 MPa, and most preferably greater than about 3.5 MPa, or the topcoat exhibits a Wear Value of greater than about 1000 $(MPa)^2$, more preferably greater than about 1250 $(MPa)^2$, even more preferably greater than about 1500 $(MPa)^2$, and most preferably greater than about 2000 $(MPa)^2$.

Properties of Films of the Present Invention

The present kits form films having defined properties which are expressed by their Peak Adhesive Strengths and Toughness Values.

Peak Adhesive Strength is a measure of the peel force required to remove a nail polish from a substrate which has been chosen to simulate the nail, under prescribed conditions of sample preparation, drying, treatment, and peeling. The present inventors have surprisingly discovered kits providing films which exhibit Peak Adhesive Strengths of greater than about 10 g/mm, more preferably greater than about 15 g/mm, even more preferably greater than about 25 g/mm, and most preferably greater than about 50 g/mm.

The present inventors have further discovered kits which provide tough, hard, chip-resistant films. Preferred kits of the present invention provide films having one or more layers (preferably the topcoat) exhibiting a Toughness Value, as described herein, of greater than about 1.2 MPa, more preferably greater than about 1.8 MPa, even more preferably greater than about 2 MPa, and most preferably greater than about 3.5 MPa, or exhibiting a Wear Value of greater than about 1000 $(MPa)^2$, more preferably greater than about 1250 $(MPa)^2$, even more preferably greater than about 1500 $(MPa)^2$, and most preferably greater than about 2000 $(MPa)^2$. Wherein a nail polish film is comprised of a single layer, the toughness of the film is measured in a reproducible manner by measuring the tensile properties of the film. Wherein a nail polish is comprised of multiple layers, the toughness or hardness of any individual layer can be measured by measuring the tensile properties of that layer individually.

In vitro Wet Adhesion Method

Fishscales of large buffalo fish are harvested and prepared as the substrate. Fresh scales are removed from the fish with a conventional scaling tool, collected and maintained under refrigeration until ready for cleaning. Scales are cleaned using dilute, mild dishwashing liquid until they are visibly free of flesh and skin. For example, in a 2 liter beaker, 1 liter of warm water (90° F.–110° F.) is mixed with 3 mL of Dawn® dishwashing liquid and the scales of a single fish are added to this mixture. The mixture is stirred by hand for one minute. The scales are allowed to settle for five minutes and then the water is decanted from the beaker. Water is added and the mixture is stirred and decanted again.

In another 2 liter beaker, 1 liter of warm water (90° F.–110° F.) is prepared with 3 mL of Dawn® dishwashing liquid as before. The scales are transferred to this mixture and all washing and decanting steps are repeated again. The scales are rinsed once more. If the water appears soapy after the final rinsing and decanting steps, rinsing is continued until the water is clear with no visible bubbles. If the scales do not appear visibly clean of flesh and skin, the process is repeated with increased agitation until they are clean. On a large, flat surface in a well ventilated area such as a fume hood, a single layer of the clean scales is spread out on paper towels. A layer of paper towels is placed over the scales and weighted on all sides to minimize curling of the scales during drying. The scales are allowed to dry for 48 hours at ambient conditions. Scales suitable for use in this method are those which exhibit an average surface energy of about 38 $mJ/m^2$ and an average polarity of about 0.26 as determined by contact angle with iodomethane and with water using the Wilhelmy plate method, calculated by the harmonic mean equation (as described by A. W. Neumann and R. J. Good, *Surface and Colloid Science*, Vol. 2, R. J. Good and R. R. Stromberg, Eds., Plenum Press (1979)). A Kruss K12 Tensiometer, or its equivalent, may be used for measurement of surface properties.

The dry scales are placed in excess warm water (90° F.–110° F.) for fifteen minutes. The scales are removed. Ten scales which meet the following criteria are selected: a) at least 18 mm in length, measured from the dark end of the scale where it was attached to the fish (hereafter designated as the bottom of the scale) to the end of the scale that is lighter in color, less thick and more flexible (hereafter designated the top of the scale); b) have a well-defined dark semi-circle that defines the bottom of the scale; and c) contain a well-defined geometric growth pattern of expanding concentric rings from the center of the scale to the edge. Scales having a diffuse pattern of lines that encompass a large portion of the center of the scale are dis'carded.

The ten scales are patted dry with a paper towel, rubbed with a dry towel to ensure removal of any debris, and placed smooth side up on a row of double sided adhesive tape which has been taped onto a coating plate. Using a standard brush-applicator, nail polish is applied immediately to the smooth side of the scales as if applying to a human fingernail, applying to the entire surface of the scale. Typically from about 0.03 to about 0.07 grams per scale per coat of nail polish is applied to each scale. For testing of kits, allow sufficient dry time (from about five to about ten minutes, testing dryness by touch) between application of the different compositions of the kits, being careful not to take so long that the scales curl at the edges before the final layer of nail polish is applied. Approximately 50 to 200 microns dry thickness, preferably 75 to 150 microns dry thickness, for 2 coats of nail polish is applied to each scale.

After application of nail polish, the coated scales are dried in a convection oven at a temperature of about 87° F. for 3 days.

After three days of drying, the coated scales are ready for measurement of peel force. The test method measures peel force on an Instron Model 1122 with Tensile Load Cell B mounted to the cross-head, operating at 500 grams full scale range. The cross-head speed should be 1.0 inches/minute. The instrument is preferably computer interfaced to collect force (in grams) and distance data. The peel force test method is based on both ASTM DI 876 (T-peel test) and ASTM D903 (180-degree peel test) with variations as described herein. Descriptions of such methods with drawings describing peel angles can also be found in *Polymer Interface and Adhesion*, S. Wu, p. 530 (1982).

The ten coated scales are cut into lengthwise strips of from about 4 mm to about 7 mm wide, one strip per scale. Each scale is first cut to one side of the middle, avoiding the hard condyle-like feature at the center of the scale, visible from the back of the scale. The outside edge of the strip is cut parallel to the first cut, and the top of the scale is trimmed slightly leaving no natural scale edges except at the bottom of the strip. Each scale is immersed in water for three hours at 70° F. The starting time for immersing the strips in water is staggered, several minutes apart per scale. After three hours the first strip is removed, carefully pat dry with a paper towel, and a free edge is created at the top of the scale by carefully impinging the top edge against a blunt surface or by drawing a hard, blunt object such as a spatula or a human fingernail across the edge, while not disturbing the majority of the coated scale. The free edge will extend across the width of the scale at the top, allowing it to be gripped with adhesive tape, but should extend a maximum of about 3 mm in the lengthwise direction. A piece of transparent adhesive tape such as conventional Scotch Tape® is firmly attached in a lengthwise direction to the coating, allowing the tape to extend several inches beyond the free edge. The free edge is carefully bent and taped back from the scale and a second piece of tape is attached to the back side of the coating free edge, thus gripping the free edge from both sides with tape. For films which exhibit less than 10 g/mm peak peel force, attachment of the second piece of tape to the back side of the free edge is omitted. The free end of the tape that extends from the top of the coated scale is attached to the cross-head by taping it to a grip or other type of transom fabricated for this purpose. The top end of the scale which has been freed from the coating is gripped with the hands or a holder firmly, at the base of the instrument, allowing some slack in the tape. The free edge of the scale must be held immovable against the base of the Instron for the entire measurement. The bottom side of the scale is supported, in a slightly elevated position, so as to create approximately a 135 degree peel angle from the substrate, but is not held in any grip.

The cross-head movement is started and force-displacement or force-time data is collected. The flexible scale substrate will naturally bend slightly during the test, creating a peel that is a cross between a conventional T-peel and a conventional 135-degree peel of a flexible coating on a rigid substrate. The measurement is continued until the peel breaks, tears, falls off, or reaches the edge of the dark portion at the scale bottom, at which point the peel is stopped. If at any time the adhesive tape pulls away from the coating or the coating tears, stop the peel immediately. If the nail polish stretches near the adhesive failure locus, so that the adhesive tape disengages itself from the polish locally, the peel must be stopped and force results obtained are discarded. The tape may optionally be reattached and results before and after disengagement of the tape collected. If less than ten seconds of continuous peel force data has been collected, measured from the onset of the steady peel as described above, then discard the result. As used herein, the maximum force obtained within the steady peel region is $F_m$. The width of the peeled strip ($W_s$) is measured in mm to the nearest $\frac{1}{10}$ mm and this is recorded with the peel force/distance data.

The Peak Adhesive Strength for a given strip (S) is calculated as follows:

$$S = F_m \div W_s$$

The foregoing peel process is repeated for the remaining scales. If less than ten acceptable peels are obtained, more samples must be tested. The Peak Adhesive Strength results for each strip are averaged for the ten scales to give the Peak Adhesive Strength for the nail polish tested, expressed in grams of force per millimeter of width.

Toughness Value and Wear Value Method

Toughness Values and Wear Values are determined in accordance with the following method. Sample preparation differs depending on whether the film-forming polymer present in the composition is water-borne or solvent-borne. Wherein a composition comprises both a water-borne and solvent-borne polymer, the below sample preparation for solvent-borne nail polish is utilized. However, if the film is insufficiently viscous or thixotropic to provide a suitable film by that drawdown method (i.e., instead of remaining spread out, it withdraws to a narrower and thicker film or even forms droplets), the water-borne procedure described below is used for film preparation.

(a) Sample Preparation for Solvent-borne Nail Polish

The nail polish to be tested is drawn down on a flat surface (e.g. a 10 inch×11 inch glass plate) covered with a double layer of Teflon® sheet (e.g., Bytac VF-81, commercially available from Norton Performance Plastics Corporation of Akron, Ohio). An abrasive emery board is used to scratch the Teflon® surface lightly on the sides, outlining a rectangular draw down area so the wet sample adheres temporarily to the Teflon® sheet while it dries (the rectangular draw down area is defined by long sides approximately the inside width of a drawdown bar and both ends). Using a 6.0 mil bird applicator draw down bar, draw down a nail polish wet film. The bird applicator bar draws a 3 inch wide coating of polish and the overall length of the bar is 4.5 inches. Such wet film applicators are available from coatings test equipment suppliers such as the Paul N. Gardner Company, Inc., Pompano Beach, Fla. If the solvent-borne film is insufficiently viscous or thixotropic to provide a suitable film by this drawdown method (i.e., instead of remaining spread out, it withdraws to a narrower and thicker film or even forms droplets), the water-borne procedure described below is used for film preparation. The remainder of the procedure for solvent-borne films is then followed (e.g., thickness evaluation and 7-day drying). Place the coated substrate in a 87° F. convection oven for five minutes.

After five minutes of drying to give a first layer, remove from the oven and clean the perimeter of the drawdown area by gently scraping away excess film from the edge with a spatula. Draw down a second coat of the same polish directly on the first layer, again using the 6 mil draw down bar. Then place the coated substrate in the 87° F. convection oven for 40 minutes.

After 40 minutes of drying remove the coated substrate from the oven, remove the films from the substrate and cut them into ½ inch wide strips using a precision film strip cutter such as a JDC Precision Sample Cutter (available from Paul N. Gardner Company, Inc. of Pompano Beach, Fla.) (or equivalent thereof which ensures the edges are the same width across the whole sample length, and smooth so as not to start a tear or other flaw/weak point in the film). Place the strips on a Teflon® covered plate pushing down gently to make good contact with the Teflon®. The strips are then returned to the 87° F convection oven until they are required for testing. Mechanical properties are tested at several time intervals between 0 and 168 hours (7 days) (time 0 [$t_0$] being the time at which the second drawdown is completed and the sample replaced into the oven to dry the second layer, time$_{test}$ being the time after $t_0$ at which the mechanical properties are tested).

Remove strips from the oven and cut into 2.25 inch lengths using the JDC Precision Sample Cutter or equivalent.

Sample preparation for water-borne nail polish: 10"×11"×¼" plexiglass boards are covered with Bytac adhesive Teflon® film. Four narrow parallel slots are cut with a razor knife into the board to remove the Bytac film from the slot area along the entire length of the board to serve as trenches which fill with excess nail polish as the polish is drawn down across the board. The slots are cut ⅛ inches wide along the length of the acrylic board. Two slots are cut about 1 inch in from the edge of the board. Two inner slots are cut about 4 inches from each edge. Each board will accommodate two 3 inch wide films.

The acrylic board is placed on a leveling table. A release coat (which is a composition consisting of 5.5 % (polymer solids) Sancure 2710, 7.9% ethanol, 78.1% ethyl acetate, and 8.5% water) is drawn down as a first step, applied with a 3 mil bird type film applicator. The release coat is applied as one layer and permitted to dry for at least five minutes, until dry to the touch.

The nail polish to be tested is applied over the release coat with a bird applicator (range of 1 mil, 3 mil, or 6 mil) to achieve a final sample average dry film thickness (as determined by digital caliper) of 0.04 mm+/−0.002 mm. Trial and error is used to determine the most suitable drawdown bar, the bird applicator is chosen to achieve this desired thickness is a function of the rheology of the sample. If the average thickness is outside this range, but a sufficient sample size of films which span this average can be run, a linear least squares regression of the resultant property data as a function of thickness may be done and the calculated results at 0.040 mm reported. The sample is permitted to dry on the leveling table at room temperature until the film is firmly set. The setup time can vary according to the nail polish tested, but is typically from about five minutes to about one hour. When film is set, the acrylic board is placed in an 87° F. convection oven for 48 hours to dry.

Remove the board from the oven and remove the film from the board by cutting the film around its perimeter with a razor knife. The film is then easily lifted off the board and is cut into ½ inch wide strips using the JDC Precision Sample Cutter or equivalent. The strips are cut into 2.25 inch lengths.

The remainder of the method is applicable to both solvent-borne and water-borne systems.

(b) Testing

Affix a 1 inch piece of Scotch brand tape to each end of the strip (approximately 0.125" into the sample) and fold it over on itself to produce half inch "taped ends" with a non-taped sample length of 2 inches. Measure the thickness of the film strip to be tested using a micrometer (e.g. Mitutoyo micrometer). The thickness is measured to the nearest 0.001 mm by averaging the thickness of 5 spots evenly distributed along the length of the film. If the average measured film thickness is between 0.04 and 0.05 mm then proceed with the test. If not, modify the drawdown procedure given above for the nail polish being tested in order to bring its dry film thickness to within the 0.04 to 0.05 mm range (i.e., additional coats can be applied if the film is too thin; fewer coats and/or a 3 mil draw-down bar may be substituted if the film is too thick)

The mechanical properties of the film strips are measured on a calibrated Instron 4500 series apparatus (or equivalent thereof) using Instron Series IX software for Windows (Merlin version) (or equivalent thereof). Both the equipment and software are commercially available from Instron Corp., Canton, Mass. In the test, the Instron measures force as a function of applied tensile strain. A 100 N static load cell, a 2.0 inch gauge length, at a crosshead speed of not less than 2 and not greater than 20 inches travel/minute is used. Pneumatic action jaws at a minimum 40 PSI air pressure are used with 1 inch×0.5 inch smooth rubber coated faces to hold the test film (available from Instron Corp., Canton, Mass.).

The Series IX software is automatically programmed to report strain (mm/mm), Young's modulus (MPa) and toughness (MPa). "Strain" is measured as film elongation (mm/mm) to break; "Young's modulus" is the initial slope of the stress/strain curve; "toughness" is measured as the area under the stress/strain curve to break, which is equal to the energy to break divided by the sample volume, reported elsewhere in various units such as kgfmm/mm$^3$ or also psi.

The Instron is calibrated and checked at the start of the experiment with dead weights to ensure accuracy. Appropriate data for the film (for example, thickness, width, gauge length, and sample number) are entered into the computer and a film strip is loaded into the grips, being careful not to damage the film while loading, especially at the grips. The taped ends of the film are used to provide a reinforcement for the part of the film within the grips. Avoid direct contact with the films to eliminate possible contamination from skin oils which may influence results. In order to present a film exactly parallel to the direction of the pull, with no wrinkles, use of a simple guide may be necessary.

Begin the tensile test and run until the film breaks. Watch the film during the run to ensure the film does not break at the grips or at a film flaw. If either of these occur, discard the data for that strip. Repeat the process for all film strips. At least six sample pulls are obtained for each nail polish sample, more if needed to develop a reproducible, average result (the Young's Modulus should have a standard error of the mean of less than about 5%). The average break strain, Young's Modulus and toughness of the film to break are calculated from all of the samples for each time point of interest, and reported as the % Strain (mm/mm), Rigidity Value (MPa), and Toughness Value (MPa), respectively. The Wear Value is obtained by multiplying the Rigidity Value by the Toughness Value.

Equivalents to this hardware/software must be thoroughly evaluated because there are many known differences from machine to machine. In order to ensure reproducibility of results from machine to machine, a standard plastic test strip is run to ensure both hardware and software are working according to specifications. Polyethylene bags measuring 6"×8"0.002" by Loc-Top, (commercially available as Catalog No. ML-68NC from ResourceNet, Cincinnati, Ohio) (or equivalent thereof), are used as a standard plastic test film for tensile tests. These are cut into ½ inch strips cutting parallel to the top opening. The strips are run at a length of 6 inches (i.e., not cut to size); gauge length remains 2 inches. The sample is loaded and tested as above. Table I below shows typical results for the plastic strips.

TABLE I

| Parameter | Result |
| --- | --- |
| Thickness | 0.0395 mm (+/−2%) |
| Peak Stress | 29.8 MPa (+/−5%) |
| Maximum Strain | 2.1 mm/mm (+/−5%) |
| Young's Modulus | 238 MPa (+/−3%) |
| Toughness Value at Break | 48.2 MPa (+/−11%) |
| Cross-head Speed | 2 to 20 inches/minute |

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

In the examples herein below, all polymer component percentages are expressed in weight percent of solid polymer (based on the total composition).

Examples 1A–1H

The compositions of Examples 1A–1H are representative of basecoat compositions of the present invention:

|  | Ex. 1A | Ex. 1B | Ex. 1C | Ex. 1D | Ex. 1E | Ex. 1F | Ex. 1G | Ex. 1H |
| --- | --- | --- | --- | --- | --- | --- | --- | --- |
| Sancure 2710 ® | 5.5% | 4% | 5.8% | 5.81% | 5.4% | — | 5.74% | 5.74% |
| Glascol LS20 ® | — | — | — | — | 5.7% | — | — | — |
| NeoRez R967 ® | — | — | — | — | — | 5.87% | — | — |
| Ethanol | 7.9% | — | — | — | — | — | — | — |
| iso-Propanol | — | — | — | 32.13% | 44.9% | 65.8% | 65.83% | 46.99% |
| Ethyl Acetate | 78.1% | — | — | — | — | — | — | — |
| n-Propanol | — | 71.6% | 70% | — | — | — | — | — |
| Methyl Paraben | — | — | 0.1% | 0.21% | — | 0.1% | 0.2% | 0.2% |
| Propyl Paraben | — | — | 0.1% | — | 0.2% | — | — | — |
| Water | 8.5% | 24.4% | 24% | 61.85% | 43.8% | 28.23% | 28.23% | 47.07% |

Examples 2A–2E

The compositions of Examples 2A–2E are representative of topcoat compositions of the present invention:

|  | Ex. 2A | Ex. 2B | Ex. 2C | Ex. 2D | Ex. 2E |
|---|---|---|---|---|---|
| Duraplus 2 ® | 21% | — | — | 21% | — |
| Nitrocellulose RS ¼ second | — | 15% | — | — | 6.75% |
| Sanres ® EX499 | — | 3.6% | — | — | — |
| Sanres ® 12711 | — | 1.5% | 15.5% | — | — |
| Sanres ® 6012 | — | — | — | — | 8.25% |
| Surcol ® 441 | — | — | 4.5% | — | — |
| Dowanol DPnP ® | 10% | — | — | 10% | — |
| Dibutyl Phthalate | 3.9% | — | — | 1.6% | — |
| Glide 450 ® | 0.3% | — | — | 0.3 | — |
| Aculyn 44 ® | 0.5% | — | — | — | — |
| Polytex E-75 (Estron Chemical) | — | 1% | — | — | — |
| Drewax E-3030 ® | — | — | — | 1.2% | — |
| Paraplex G-50 ® | — | 7.6% | — | — | — |
| Butyl Acetate | — | 32.9% | 30% | — | 40% |
| Ethyl Acetate | — | 27.4% | 10% | — | — |
| iso-Propanol | — | 11% | 30% | — | 35% |
| Toluene | — | — | — | — | 10% |
| Acetone | — | — | 10% | — | — |
| Water | 64.3% | — | — | 65.9% | — |

Example 3

The following composition may be used as either a midcoat compostion or a topcoat composition.

| Component | Supplier Slurry Code* | Source | Percentage |
|---|---|---|---|
| Solid Nitrocellulose RS ¼ second (available as a slurry) | 50-C3-690 | Akzo Nobel, Somerset, NJ | 7.05% |
| Solid Nitrocellulose RS ½ second (available as a slurry) | 5528 | Scholle Corp., College Park, GA | 7.00% |
| Clay** (available as a slurry) | Bentone slurry NJ | Kirker Enterprises Inc., Paterson, | 1.04% |
| Red #7 Solid (available as a slurry) | Red #7 slurry 6R381 | Penn Color, Doylestown, PA | 0.60% |
| Butyl Acetate |  | J. T. Baker, Phillipsburg, NJ | 27.77% |
| Ethyl Acetate |  | J. T. Baker, Phillipsburg, NJ | 24.00% |
| iso-Propanol |  | J. T. Baker, Phillipsburg, NJ | 6.55% |
| Uniplex 600 |  | Unitex, Greensboro, NC | 11.12% |
| Toluene |  | E.M. Science, Gibbstown, NJ | 6.44% |
| Camphor |  | Universal Preservachem, Edison, NJ | 1.43% |
| Dibutyl Phthalate |  | Eastman Kodak, Kingsport, TN | 7.00% |
| Total |  |  | 100% |

*The slurries contain, in addition to the component indicated, other components which are listed in the above formula (such as, for example, butyl acetate and iso-propanol). The percentage given for each component is the percentage of that component only (for example, Solid Nitrocellulose RS ¼ second is present in the control formula at a solids level of 7.05%, exclusive of other components). The levels of the other components in each slurry are combined and reflected in the formula given above. For example, the levels of butyl acetate in Nitrocellulose RS ¼ second slurry, Nitrocellulose RS ½ second slurry, clay, and Red #7 Solid are combined and reflected in the percentage given for the butyl acetate component.
**Clay is 50/50 (weight percent ratio) stearalkonium hectorite/stearalkonium bentonite solids. The composition of Example 3 may be prepared as follows. Weigh all components together into a sealable jar to hold a 100 gram batch with minimal head-space. Add six stainless steel balls, each of which are 3/16 inches in diameter. Mix on a conventional paint shaker for thirty minutes. Transfer to conventional nail polish bottles.

Example 4

A kit comprising two separate nail polish compositions is prepared. The compositions are a basecoat composition of Example 1 and a topcoat composition of Example 2. The basecoat composition is applied contiguously to mammalian nails using a standard brush-applicator. A basecoat is allowed to form over a period of five minutes. The topcoat composition is applied contiguously to the basecoat using a standard brush-applicator. The topcoat composition is allowed to form a topcoat over a five minute time period, resulting in a film having two layers.

Example 5

A kit comprising two separate nail polish compositions is prepared. The compositions are a basecoat composition of Example 1 and a topcoat composition which is a conventional nail polish such as Max Factor®0 International (comprising butyl acetate, ethyl acetate, nitrocellulose, toluenesulfonamide formaldehyde resin, dibutyl phthalate, toluene, iso-propanol, camphor, benzophenone, stearalkonium hectorite, and polyester resin). The basecoat composition is applied contiguously to mammalian nails using a standard brush-applicator. A basecoat is allowed to form over a period of five minutes. The topcoat composition is applied contiguously to the basecoat using a standard brush-applicator. The topcoat composition is allowed to form a topcoat over a five minute time period, resulting in a film having two layers.

Example 6

A kit comprising two separate nail polish compositions is prepared. The compositions are a basecoat composition which is a conventional nail polish, such as Max Factor® International (comprising butyl acetate, ethyl acetate, nitrocellulose, toluenesulfonamide formaldehyde resin, dibutyl phthalate, toluene, iso-propanol, camphor, benzophenone, stearalkonium hectorite, and polyester resin) and a topcoat composition of Example 2. The basecoat composition is applied contiguously to mammalian nails using a standard brush-applicator. A basecoat is allowed to form over a period of five minutes. The topcoat composition is applied contiguously to the basecoat using a standard brush-applicator. The topcoat composition is allowed to form a topcoat over a five minute time period, resulting in a film having two layers.

Example 7

A kit comprising three separate nail polish compositions is prepared. The compositions are a basecoat composition of Example 1, a midcoat composition which is a conventional nail polish, such as Max Factor® International (comprising butyl acetate, ethyl acetate, nitrocellulose, toluenesulfonamide formaldehyde resin, dibutyl phthalate, toluene, isopropanol, camphor, benzophenone, stearalkonium hectorite, and polyester resin) and a topcoat composition of Example 2. The basecoat composition is applied contiguously to mammalian nails using a standard brush-applicator. A basecoat is allowed to form over a period of five minutes. The midcoat composition is applied contiguously to the basecoat using a standard brush-applicator. The midcoat composition is allowed to form a layer over a period of five minutes, resulting in a film having two layers. The topcoat composition is applied contiguously to the layer formed from the midcoat composition using a standard brush-applicator. The topcoat composition is allowed to form a topcoat over a period of five minutes, providing a film having three layers.

Example 8

A kit comprising two separate nail polish compositions is prepared. The compositions are a basecoat composition of Example 1 and a topcoat composition as set forth in Example 3. The basecoat composition is applied contiguously to mammalian nails using a standard brush-applicator. A basecoat is allowed to form over a period of five minutes. The topcoat composition is applied contiguously to the basecoat using a standard brush-applicator. The topcoat composition is allowed to form a topcoat over a five minute time period, resulting in a film having two layers.

What is claimed is:

1. A nail polish film comprising two or more different layers wherein the film exhibits a Peak Adhesive Strength of greater than about 25 g/mm.

2. A film according to claim 1 comprising a topcoat exhibiting a Toughness Value of greater than about 1.2 MPa or a Wear Value of greater than about 1000 $(MPa)^2$.

3. A film according to claim 2 comprising a basecoat and the topcoat wherein:
   (a) the basecoat comprises a film-forming water-insoluble polymer selected from the group consisting of polyurethanes, polyacryls, polymethacryls, urethane-acryl copolymers, styrene-acryl copolymers, and mixtures thereof; and
   (b) the topcoat comprises a film-forming water-insoluble polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

4. A film according to claim 1 comprising a basecoat and a topcoat wherein:
   (a) the basecoat comprises a film-forming water-insoluble polymer selected from the group consisting of polyurethanes, polyacryls, polymethacryls, urethane-acryl copolymers, styrene-acryl copolymers, and mixtures thereof; and
   (b) the topcoat comprises a film-forming water-insoluble polymer selected from the group consisting of cellulosic polymers, polyurethanes, polyacryls, polymethacryls, polysiloxanes, and mixtures thereof.

5. A film according to claim 2 comprising a basecoat and the topcoat wherein:
   (a) the basecoat comprises a film-forming water-insoluble polymer selected from the group consisting of cellulosic polymers, polyurethanes, polyacryls, polymethacryls, polysiloxanes, and mixtures thereof; and
   (b) the topcoat comprises a film-forming water-insoluble polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

6. A film according to claim 3 further comprising a midcoat comprising a film-forming water-insoluble polymer selected from the group consisting of cellulosic polymers, polyurethanes, polyacryls, polymethacryls, polysiloxanes, and mixtures thereof.

7. A film according to claim 2 wherein the Toughness Value is greater than about 1.8 MPa and the Wear Value is greater than about 1250 $(MPa)^2$.

8. A kit suitable for use as a nail polish for mammalian nails, the kit comprising two or more different compositions, wherein the compositions when applied to the nail form a film exhibiting a Peak Adhesive Strength of greater than about 25 g/mm.

9. A kit according to claim 8 comprising a topcoat composition which, when applied to the nail, forms a topcoat exhibiting a Toughness Value of greater than about 1.2 MPa or a Wear Value of greater than about 1000 $(MPa)^2$.

10. A kit according to claim 9 wherein the polymer is selected from the group consisting of polyurethanes, polyacryls, polymethacryls, cellulosic polymers, styrene-acryl copolymers, polystyrene-polyacryl mixtures, polysiloxanes, polyesters, urethane-acryl copolymers, siloxane-urethane copolymers, polyurethane-polymethacryl mixtures, silicone-acryl copolymers, vinyl acetate polymers, and mixtures thereof.

11. A kit according to claim 8 comprising a basecoat composition comprising a water-insoluble film-forming polymer selected from the group consisting of polyurethanes, polyacryls, polymethacryls, urethane-acryl copolymers, styrene-acryl copolymers, and mixtures thereof.

12. A kit according to claim 11 wherein the basecoat composition comprises a water-insoluble film-forming polyurethane.

13. A kit according to claim 10 comprising a topcoat composition comprising a water-insoluble film-forming polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

14. A kit according to claim 9 comprising a basecoat composition and the topcoat composition wherein:
   (a) the basecoat composition comprises a film-forming water-insoluble polymer selected from the group consisting of polyurethanes, polyacryls, polymethacryls, urethane-acryl copolymers, styrene-acryl copolymers, and mixtures thereof; and (b) the topcoat composition comprises a film-forming water-insoluble polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

15. A kit according to claim 8 comprising a basecoat composition and a topcoat composition wherein:

(a) the basecoat composition comprises a film-forming water-insoluble polymer selected from the group consisting of polyurethanes, polyacryls, polymethacryls, urethane-acryl copolymers, styrene-acryl copolymers, and mixtures thereof; and (b) the topcoat composition comprises a film-forming water-insoluble polymer selected from the group consisting of cellulosic polymers, polyurethanes, polyacryls, polymethacryls, polysiloxanes, and mixtures thereof.

16. A kit according to claim 9 comprising a basecoat composition and the topcoat composition wherein:

(a) the basecoat composition comprises a film-forming water-insoluble polymer selected from the group consisting of cellulosic polymers, polyurethanes, polyacryls, polymethacryls, polysiloxanes, and mixtures thereof; and (b) the topcoat composition comprises a film-forming water-insoluble polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

17. A kit according to claim 14 further comprising a midcoat composition comprising a film-forming water-insoluble polymer selected from the group consisting of cellulosic polymers, polyurethanes, polyacryls, polymethacryls, polysiloxanes, and mixtures thereof.

18. A kit according to claim 9 wherein the Toughness Value is greater than about 1.8 MPa and the Wear Value is greater than about 1250 $(MPa)^2$.

19. A kit according to claim 9 further comprising information that use of the kit provides one or more long wear benefits.

20. A method of coating mammalian nails with a nail polish film, the film comprising two or more layers, wherein the method comprises the steps of:

(a) applying a basecoat composition contiguously to the nail, wherein the basecoat composition comprises a film-forming polymer and a liquid diluent;

(b) removing sufficient liquid diluent from the basecoat composition to form a substantially dry basecoat;

(c) applying a topcoat composition to the nail, wherein the topcoat composition comprises a film-forming polymer and a liquid diluent; and (d) removing sufficient liquid diluent from the topcoat composition to form a substantially dry topcoat;

wherein the film exhibits a Peak Adhesive Strength of greater than about 25 g/mm.

21. A method according to claim 20 wherein the topcoat exhibits a Toughness Value of greater than about 1.2 MPa or a Wear Value of greater than about 1000 $(MPa)^2$.

* * * * *